United States Patent [19]

Allais et al.

[11] 4,096,260
[45] Jun. 20, 1978

[54] NOVEL INDOLES

[75] Inventors: André Allais, Gagny; Jean Meier, La Varenne Saint-Hilaire; Roger Deraedt, Pavillons-sous-Bois, all of France

[73] Assignee: Roussel Uclaf, Paris, France

[21] Appl. No.: 760,107

[22] Filed: Jan. 17, 1977

[30] Foreign Application Priority Data

Jan. 21, 1976 France .................. 76 01561

[51] Int. Cl.² .................. A61K 31/495; C07D 295/14
[52] U.S. Cl. .................. 424/250; 544/373
[58] Field of Search .................. 260/268 BC; 424/250

[56] References Cited

U.S. PATENT DOCUMENTS 3,856,967  12/1974  Allais et al. .................. 424/274
3,985,878  10/1976  Makovec et al. .................. 260/268 BC Primary Examiner—Paul M. Coughlan, Jr.
Attorney, Agent, or Firm—Hammond & Littell

[57] ABSTRACT

Novel indoles of the formula

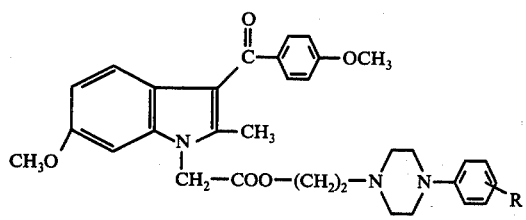

wherein R is in the 2-, 3- or 4-position and is selected from the group consisting of hydrogen, halogen, —CF₃, —SCF₃, —OCF₃ and alkyl and alkoxy of 1 to 8 carbon atoms and their non-toxic, pharmaceutically acceptable acid addition salts having analgesic activity.

12 Claims, No Drawings

NOVEL INDOLES

STATE OF THE ART

U.S. Pat. No. 3,856,967 and French Pat. Nos. 2,002,284 and No. 2,280,379 disclose various 1-carboxyalkyl-2-methyl-indoles having anti-inflammatory and analgesic activity.

OBJECTS OF THE INVENTION

It is an object of the invention to provide the novel indoles of formula I and their non-toxic, pharmaceutically acceptable acid addition salts and their preparation.

It is another object of the invention to provide novel analgesic compositions and to provide a novel method of relieving pain in warm-blooded animals.

These and other objects and advantages of the invention will become obvious from the following detailed description.

THE INVENTION

The novel products of the invention are selected from the group consisting of indoles of the formula

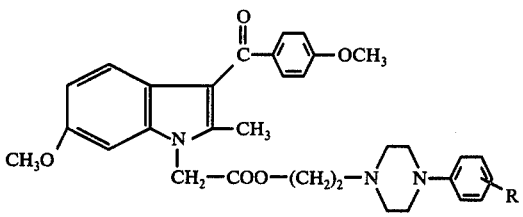

wherein R is in the 2-, 3- or 4-position and is selected from the group consisting of hydrogen, halogen, —CF$_3$, —SCF$_3$, —OCF$_3$ and alkyl and alkoxy of 1 to 8 carbon atoms and their non-toxic, pharmaceutically acceptable acid addition salts.

When R is halogen, it is preferably chlorine, fluorine or bromine and when R is alkyl or alkoxy it is preferably methyl, ethyl, n-propyl, n-butyl, methoxy, ethoxy, n-propoxy or n-butoxy. A preferred group of compounds are those when R is CF$_3$, chlorine or hydrogen and their non-toxic, pharmaceutically acceptable acid addition salts.

The two specific preferred compounds are 2-[4-(3-trifluoromethylphenyl)-1-piperazinyl]-ethyl 3-(4-methoxyphenylcarbonyl)-6-methoxy-2-methyl-1-[1H]-indoleacetate and 2-[4-phenyl-1-piperazinyl]-ethyl 3-(4-methoxyphenylcarbonyl)-6-methoxy-2-methyl-1-[1H]-indoleacetate and their non-toxic, pharmaceutically acceptable acid addition salts, particularly the hydrochloride.

Examples of suitable acids for the preparation of the non-toxic, pharmaceutically acceptable salts are mineral acids such as hydrochloric acid, hydrobromic acid, sulfuric acid or phosphoric acid or organic acids such as acetic acid, citric acid or propionic acid or sulfonic acids such as methane sulfonic acid or p-toluene sulfonic acid.

The process of the invention for the preparation of the products of formula I comprises reacting a compound of the formula

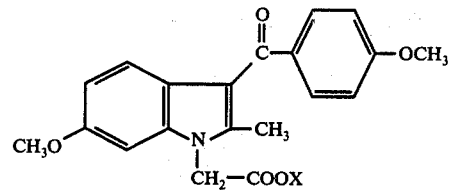

wherein X is alkyl of 1 to 8 carbon atoms with a compound of the formula

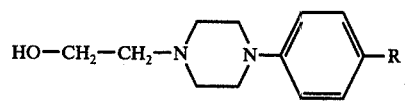

wherein R has the above definition to obtain the corresponding compound of formula I which may be treated with an acid to form the acid addition salt.

In a preferred mode of the process of the invention, X is methyl, ethyl, n-propyl or n-butyl and the transesterification is effected in the presence of an alkaline agent such as an alkali metal hydride, amide or alcoholate. The reaction is preferably effected in an organic solvent at a temperature of 50° to 200° C.

The compounds of formula II may be made by the process of French Pat. No. 1,584,808 and the compounds of formula III may be made by the process of French Pat. No. 2,141,526.

The novel analgesic compositions of the invention are comprised of an analgesically effective amount of at least one compound of formula I and its non-toxic, pharmaceutically acceptable acid addition salts and an inert pharmaceutical carrier. The compositions may be in the form of tablets, dragees, gelules, granules, suppositories, injectable solutions or suspensions, pomades, creams, gels and aerosol preparations.

The pharmaceutical carrier may be those conventionally used such as talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions due to their analgesic activity are useful for the treatment of muscular, articular or nervous pains, dental pains and migraines.

The novel method of the invention for relieving pain in warm-blooded animals, including humans, comprises administering to warm-blooded animals an analgesically effective amount of at least one compound of formula I and its non-toxic, pharmaceutically acceptable acid addition salts. The compounds may be administered orally, rectally, parenterally or topically to the skin and mucous. The usual effective dose depends on the method of administration and the specific compound. For example, the effective daily dose in the adult is 0.4 to 40 mg/kg by the oral way.

In the following examples there are described several preferred embodiments to illustrate the invention. However, it should be understood that the invention is not intended to be limited to the specific embodiments.

EXAMPLE 1

2-[4-(3-trifluoromethylphenyl)-1-piperazinyl]-ethyl6-methoxy-3-(4-methoxyphenylcarbonyl)-2-methyl-1-[1H]-indoleacetate hydrochloride 150 mg of a 50% suspension of sodium hydride in oil were added with stirring under a nitrogen current to a mixture of 7.3 g of methyl 6-methoxy-3-(4-methoxyphenylcarbonyl)-2-methyl-1-[1H]-indoleacetate and 6.13 g of (3-trifluoromethylphenyl)-piperazinyl ethanol in 50 ml of anhydrous toluene and the mixture was refluxed for 21 hours while removing the methanol formed. The solvent was evaporated under reduced pressure to obtain 13.35 g of residue which was dissolved in 100 ml of methylene chloride. The solution was made alkaline by addition of triethylamine and the resulting product was chromatographed over silica gel. Elution was effected with methylene chloride containing 5% of triethylamine and the residue was dissolved in 25 ml of hot acetone. The solution was iced and filtered and the filtrate was evaporated to dryness. The residue was dissolved in 100 ml of methylene chloride. The solution was washed with water until neutral, then dried. The solvent was evaporated. The residue was dissolved in 25 ml of hot ethanol and 4.7 of an ethanolic solution of 5.17 N hydrochloric acid were added. The solution was iced and the recovered precipitate was crystallized from ethanol to obtain 7.45 g of 2-[4-(3-trifluoromethylphenyl)-1-piperazinyl]-ethyl 6-methoxy-3-(4-methoxy phenylcarbonyl)-2-methyl-1-[1H]-indoleacetate hydrochloride melting at 173°–175° C.

EXAMPLE 2

2-[4-phenyl-1-piperazinyl]-ethyl 6-methoxy-3-(4-methoxyphenylcarbonyl)-2-methyl-1-[1H]-indoleacetate hydrochloride Using the procedure of Example 1, 7.35 g of methyl 6-methoxy-3-(4-methoxyphenylcarbonyl)-2-methyl-1-[1H]-indoleacetate and 4.64 g of phenylpiperazinyl ethanol in 50 ml of anhydrous toluene were reacted to obtain 4.5 g of 2-[4-phenyl-1-piperazinyl]-ethyl 6-methoxy-3-(4-methoxyphenylcarbonyl)-2-methyl-1-[1H]-indoleacetate hydrochloride melting at 132° C.

Analysis: $C_{32}H_{35}N_3O_5 \cdot HCl$; molecular weight = 578.11 Calculated: %C, 66.48; %H, 6.27; %N, 7.26; %Cl, 6.13. Found: %C, 66.3; %H, 6.1; %N, 7.1; %Cl, 5.9.

EXAMPLE 3

Tablets were prepared containing 50 mg of the product of Example 1 and sufficient excipient of lactose, starch, talc and magnesium stearate to obtain a final tablet weight of 350 mg.

PHARMACOLOGICAL DATA

Analgesic Activity

The test used was based on the test of Koster et al [Fed. Proc., Vol. 18 (1959) p. 412] in which the intraperitoneal injection of acetic acid provoked in mice repeated stretching and twisting movements which persisted for more than 6 hours. An analgesic prevents or diminishes this syndrone which is considered an exteriorization of a diffuse abdominal pain.

The acetic acid was administered as a 1% aqueous solution and the dose which released this syndrome was 0.01 ml/g or 100 mg/kg of acetic acid. The test products A (product of Example 1) and B (product of Example 2) were orally administered 30 minutes before the acetic acid injection and the animals were fasted for 24 hours before the test. The number of stretchings were observed and counted for each mouse over 15 minutes starting right after the acetic acid injection. The results were expressed as $DA_{50}$ which is the dose permitting a 50% reduction in the number of stretchings as compared to the control animals. The $DA_{50}$ dose was 2 and 20 mg/kg for products A and B, respectively.

Various modifications of the products and methods of the invention may be made without departing from the spirit or scope thereof and it is to be understood that the invention is intended to be limited only as defined in the appended claims.

We claim:

1. A compound selected from the group consisting of indoles of the formula

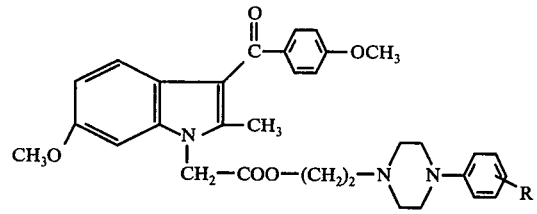

wherein R is in the 2-, 3- or 4-position and is selected from the group consisting of hydrogen, halogen, —CF₃, —SCF₃, —OCF₃ and alkyl and alkoxy of 1 to 8 carbon atoms and their non-toxic, pharmaceutically acceptable acid addition salts.

2. A compound of claim 1 wherein R is selected from the group consisting of hydrogen, chlorine and —CF₃.

3. A compound of claim 1 selected from the group consisting of 2-[4-(3-trifluoromethylphenyl)-1-piperazinyl]-ethyl 6-methoxy-3-(4-methoxyphenylcarbonyl)-2-methyl-1-[1H]-indoleacetate and its non-toxic, pharmaceutically acceptable acid addition salts.

4. A compound of claim 1 selected from the group consisting of 2-[4-phenyl-1-piperazinyl]-ethyl 6-methoxy-3-(4-methoxyphenylcarbonyl)-2-methyl-1-[1H]-indoleacetate and its non-toxic, pharmaceutically acceptable acid addition salts.

5. A compound of claim 1 which is 2-[4-(3-trifluoromethylphenyl)-1-piperazinyl]-ethyl 6-methoxy-3-(4-methoxyphenylcarbonyl)-2-methyl-1-[1H]-indoleacetate hydrochloride.

6. An analgesic composition comprising an analgesically effective amount of at least one compound of claim 1 and an inert pharmaceutical carrier.

7. A composition of claim 6 wherein the compound is selected from the group consisting of 2-[4-(3-trifluoromethylphenyl)-1-piperazinyl]-ethyl 6-methoxy-3-(4-methoxyphenylcarbonyl)-2-methyl-1-[1H]-indoleacetate and its non-toxic, pharmaceutically acceptable acid addition salts.

8. A composition of claim 6 wherein the compound is 2-[4-(3-trifluoromethylphenyl)-1-piperazinyl]-ethyl 6-methoxy-3-(4-methoxyphenylcarbonyl)-2-methyl-1-[1H]-indoleacetate hydrochloride.

9. A method of relieving pain in warm-blooded animals comprising administering to warm-blooded animals an analgesically effective amount of at least one compound of claim 1.

10. The method of claim 9 wherein the compound is selected from the group consisting of 2-[4-(3-trifluoromethylphenyl)-1-piperazinyl]-ethyl 6-methoxy-3-(4-methoxyphenylcarbonyl)-2-methyl-1-[1H]-indoleacetate and its non-toxic, pharmaceutically acceptable acid addition salts.

11. The method of claim 9 wherein the compound is 2-[4-(3-trifluoromethylphenyl)-1-piperazinyl]-ethyl 6-methoxy-3-(4-methoxyphenylcarbonyl)-2-methyl-1-[1H]-indoleacetate hydrochloride.

12. The method of claim 9 wherein the compound is administered orally.

* * * * *